United States Patent
Vazquez Rojas et al.

(10) Patent No.: US 9,277,981 B2
(45) Date of Patent: Mar. 8, 2016

(54) DEVICE AND METHOD FOR INSERTING OR OBTAINING A FLUID WITH GAMETES, EMBRYOS OR ANY OTHER TYPE OF SOLUTION IN THE OVIDUCT OF A SOW

(75) Inventors: Juan Maria Vazquez Rojas, Murcia (ES); Emilio Martinez Garcia, Murcia (ES); Jose Luis Vazquez Rojas, Murcia (ES); Jorge Roca Aleu, Murcia (ES)

(73) Assignee: Universidad De Murcia, Murcia (ES)

( * ) Notice: Subject to any disclaimer, the term of this patent is extended or adjusted under 35 U.S.C. 154(b) by 997 days.

(21) Appl. No.: 13/132,518

(22) PCT Filed: Sep. 24, 2009

(86) PCT No.: PCT/ES2009/070402
§ 371 (c)(1),
(2), (4) Date: Oct. 3, 2011

(87) PCT Pub. No.: WO2010/034871
PCT Pub. Date: Apr. 1, 2010

(65) Prior Publication Data
US 2012/0022402 A1  Jan. 26, 2012

(30) Foreign Application Priority Data
Sep. 26, 2008 (ES) .................................. 200802740

(51) Int. Cl.
*A61D 19/04* (2006.01)
*A61D 19/02* (2006.01)
(Continued)

(52) U.S. Cl.
CPC ............ *A61D 19/04* (2013.01); *A61B 10/0045* (2013.01); *A61B 10/0291* (2013.01); *A61D 19/027* (2013.01); *A61B 17/3478* (2013.01); *A61B 2019/082* (2013.01)

(58) Field of Classification Search
CPC .... A61B 17/42; A61B 17/425; A61B 17/435; A61B 10/0045; A61B 10/04; A61B 10/045; A61D 19/00; A61D 19/02; A61D 19/027; A61D 19/04; A61M 5/315; A61M 5/3286; A61M 5/065
USPC .......... 600/33–35; 604/27, 28, 35, 36, 38, 48, 604/93.01, 164.01, 506
See application file for complete search history.

(56) References Cited

U.S. PATENT DOCUMENTS

| | | |
|---|---|---|
| 3,805,784 A | 4/1974 | Alter |
| 4,136,695 A | 1/1979 | Dafoe |

(Continued)

FOREIGN PATENT DOCUMENTS

| | | |
|---|---|---|
| AU | 75068/87 A | 1/1988 |
| AU | 599996 B2 | 8/1990 |

(Continued)

OTHER PUBLICATIONS

Polge C. "Fertilization in the Pig and Horse." J. Reprod. Fert. 54 (1978): 461-470. PubMed. Web. May 29, 2014.*

(Continued)

*Primary Examiner* — Charles A Marmor, II
*Assistant Examiner* — Carrie R Dorna
(74) *Attorney, Agent, or Firm* — Craig R. Miles; CR MILES, P.C.

(57) ABSTRACT

The device comprises an injection system, which is made up of a rigid external tubular body (1) that enables it to be inserted into the abdominal cavity of a sow. This body is, in turn, covered by a sterile sleeve (2) that enables it to be used in different animals. A flexible duct (3) runs coaxially and its distal end connects with a bevelled needle (4) that permits insertion in the oviduct (12) at an angle of 45°. The proximal end of the flexible tube connects with a device (6) that includes a sheath (7) closed at the other end by a piston (8) that slides along the inside of the sheath and that enables the precision insertion of low-volume liquids.

12 Claims, 3 Drawing Sheets

(51) Int. Cl.

| | |
|---|---|
| A61B 10/00 | (2006.01) |
| A61B 10/02 | (2006.01) |
| A61B 17/34 | (2006.01) |
| A61B 19/08 | (2006.01) |

(56) References Cited

U.S. PATENT DOCUMENTS

| | | | |
|---|---|---|---|
| 4,173,227 A | | 11/1979 | Cassou et al. |
| 4,174,715 A | * | 11/1979 | Hasson .................. 606/206 |
| 4,453,936 A | | 6/1984 | Cassou |
| 4,653,475 A | | 3/1987 | Seike et al. |
| 4,700,694 A | | 10/1987 | Shishido |
| 4,846,785 A | * | 7/1989 | Cassou et al. ............... 600/34 |
| 6,695,767 B2 | | 2/2004 | Martinez Garcia et al. |
| 2003/0212307 A1 | | 11/2003 | Hladky |
| 2005/0228225 A1 | | 10/2005 | Hauschild et al. |
| 2007/0239115 A1 | | 10/2007 | Cecchi |
| 2010/0179377 A1 | * | 7/2010 | Hagby ....................... 600/33 |

FOREIGN PATENT DOCUMENTS

| | | |
|---|---|---|
| CN | 201046152 Y | 4/2008 |
| EP | 0 093 630 A1 | 11/1983 |
| EP | 0153190 A1 | 8/1985 |
| EP | 0214043 A1 | 3/1987 |
| EP | 1177776 A1 | 6/2002 |
| ES | 2 156 579 A1 | 6/2001 |
| FR | 2603796 A1 | 3/1988 |
| WO | 0228311 A1 | 4/2002 |
| WO | 03084584 A2 | 10/2003 |
| WO | 2004100797 A1 | 11/2004 |
| WO | 2010034871 A1 | 4/2010 |

OTHER PUBLICATIONS

Australian Examination Report dated Oct. 17, 2013, issued in related AU Patent Application No. 2009295755 (3 pages).
Russian Office Action dated Oct. 3, 2013, issued in related RU Patent Application No. 2011116310 (5 pages).
Singapore Examination Report dated Nov. 19, 2013, issued in related SG Application No. 201102922-0 (8 pages).
Russian Official Action dated May 27, 2013 in corresponding RU Patent Application No. 201116310.
Colombian Notice of Partial Grant dated May 22, 2013 in corresponding CO Patent Application No. 11-50706.
Colombian Office Action dated Jan. 22, 2013 in corresponding CO Patent Application No. 11-50706.
Singapore Office Action dated Jan. 8, 2013 in corresponding SG Patent Application No. 201102922.
Ukraine Decision to Grant Patent dated Sep. 21, 2012 in corresponding UA Patent Application No. a 201105329.
South Africa Notice of Acceptance dated Oct. 21, 2011 in corresponding ZA Patent Application No. 2011/03067.
Abeydeera, L. R., et al.; "Birth of Piglets Preselected for Gender Following in vitro Fertilization of in vitro Matured Pig Oocytes by X and Y Chromosone Bearing Spermatozoa Sorted by High Speed Flow Cytometry", Theriogenology, vol. 50, pp. 981-988, Jun. 24, 1998 (8 pages).
Blair, R. M., et al.; "Peri-oestrous Hormone Profiles, Embryonic Survival and Variation in Embryonic Development in Gilts and Primiparous Sows", Journal of Reproduction and Fertility, vol. 101, pp. 167-173, 1994 (7 pages).
Espe, Joel; "Elk Semem Research and Development", Minitube of America's International Center for Biotechnology, Mt. Horeb, Wisconsin, 2006 (1 page).
Garcia, E. M., et al.; "Improving the Fertilization Ability of Sex Sorted Boar Spermatozoa"; Theriogenology, vol. 68, pp. 771-778, Jun. 8, 2007 (8 pages).
Harper, John M., et al.; "Sheep Breeds and Their Wool", Wool Production School, University of California, Ukiah and Hopland, California, Hopland Field Station, pp. 1-93, Apr. 3-5, 1992 (100 pages).
Knox, R., et al.; "An Update on North American Boar Stud Practices", Theirogenology, vol. 70, pp. 1202-1208, 2008 (7 pages).
Martelli, Alessandra, et al.; "Blood Vessel Remodeling in Pig Ovarian Follicles During the Periovulatory Period: An Immunohistochemistry and SEM-Corrosion Casting Study", Reproductive Biology and Endocrinology, vol. 7, No. 72, pp. 1-14, Jul. 16, 2009 (14 pages).
Rath, D., et al.; "Low Dose Insemination Technique in the Pig"; Boar Semen Preservation IV; IVth International Conference on Boar Semen Preservation; pp. 115-118 2000 (4 pages).
Rath, D., "Low Dose Insemination in the Sow—A Review", Reproduction of Domestic Animals, vol. 37, pp. 201-205, 2002 (5 pages).
Roca, Jordi, et al.; "Survival and Fertility of Boar Spermatozoa After Freeze-Thawing in Extender Supplemented With Butylated Hydroxytoluene"; Journal of Andrology, vol. 25, No. 3, May/Jun. 2004 (9 pages).
Spinaci, Marcella, et al.; "Sperm Sorting Procedure Induces a Redistribution of Hsp70 But Not Hsp60 and Hsp90 in Boar Spermatozoa"; Journal of Andrology, vol. 27, No. 6, pp. 899-907, Nov./Dec. 2006 (9 pp.).
Valdelvira, Gosalvez LF, et al.; "Assessment of Suitable Porcine Semen for Freezing, According to the Ejaculate Characteristics in the Iberico x Landrace Breed"; Reproduction of Domestic Animals, vol. 37, No. 5, p. 282-284, Oct. 2002 (Abstract only) (1 page).
Vazquez, J. M., et al.; "Sex-sorting Sperm by Flow Cytometry in Pigs: Issues and Perspectives", Theriogenology, vol. 71, pp. 80-88, 2009 (9 pages).
Wienen, Marjet van, et al.; "Single Layer Centrifugation with Androcoll-P Can Be Scaled-Up to Process Larger Volumes of Boar Semen", Research Article, International Scholarly Research Network, ISRN Veterinary Science, vol. 2011, Article ID 548385, Nov. 3, 2010 (8 pages).
Canadian Office Action dated Jan. 3, 2013, issued in corresponding CA Application No. 2,742,409 (3 pp).
Singapore Search Report dated Jan. 22, 2014, issued in corresponding SG Application No. 201305524-9 (9 pp).
Chilean Office Action dated Jan. 29, 2014, issued in corresponding CL Application No. 1119-2011 (14 pp).
Chinese 2nd Office Action dated Feb. 7, 2014, issued in corresponding CN Application No. 200980147203.0 (8 pp).
Australian 2nd Office Action dated Mar. 3, 2014, issued in corresponding AU Application No. 2009295755 (4 pp).
European extended Search Report dated Mar. 7, 2014, issued in corresponding EP Application No. 09815714.2 (8 pp).
Chinese Office Action dated Jun. 5, 2013 in related CN Patent Application No. 200980147203 (English translation attached). 8 pages.
New Zealand First Examination Report dated Jun. 25, 2013 in related AU Patent Application No. 612183. 2 pages.
New Zealand Notice of Acceptance dated Jul. 9, 2013 in related AU Patent Application No. 592480. 1 page.
Caballero, I., et al.; "Major Proteins of Boar Seminal Plasma as a Tool for biotechnological Preservation of Spermatozoa"; Article, 2008, pp. 1352-1355, vol. 70, Theriogenology (4 pages).
Caballero, Ignacio, et al.; "PSP-I/PSP-II Spermadhesin Exert a Decapacitation Effect on Highly Extended boar Spermatozoa"; Article, 2008, pp. 505-513, vol. 32, European Academy of Andrology, International Journal of Andrology (10 pages).
Caballero, Ignacio, et al.; "Immunolocalization and Possible Functional role of PSP-I/PSP-II Heterodimer in Highly Extended Boar Spermatozoa"; Article, Dec. 2006, pp. 766-773, vol. 27 No. 6, American Society of Andrology, Journal of Andrology (8 pages).
Caballero, Ignacio, et al.; "Influence of Seminal Plasma PSP-I/PSP-IISpermadhesin on Pig Gamete Interaction"; Article, Jan. 2005, pp. 11-16, vol. 13, Zygote, Cambridge University Press (6 pages).
Caballero, Ignacio, et al.; "Does Seminal Plasma PSP-I/PSP-II Spermadhesin Modulate the Ability of Boar Spermatozoa to Penetrate Homologous Oocytes in Vitro"; Article, Dec. 2004, pp. 1004-1012, vol. 25, No. 6, Journal of Andrology (9 pages).
Calvete, Juan J., et al.; "Mapping the Heparin-Binding Domain of Boar Spermadhesins"; Article, 1996, pp. 207-211, vol. 379, Federation of European Biochemical Societies (5 pages).

(56) References Cited

OTHER PUBLICATIONS

Calvete, Juan J., et al.; "Effect of Glycosylation on the Heparin-Binding Capability of Boar and Stallion Seminal Plasma Proteins"; Article, 1995, pp. 167-173; vol. 711, Journal of Chromatography A (7 pages).
Calvete, Juan Jose, et al.; "Boar Spermadhesin PSP-II: Location of Postranslational Modifications, Herterodimer Formation with PSP-I Glycoforms and effect of Dimerization on the Ligand-Binding Capabilities of the Subunits"; Article, Apr. 1995, pp. 179-182, vol. 365, Federation of European Biochemical Societies (4 pages).
Calvete, Juan Jose, et al.; "Characterization of Two Glycosylated Boar Spermadhesins"; Aug. 1993, pp. 719-725, vol. 218, European Journal of Biochemistry (7 pages).
Campanero-Rhodes, Maria A., et al.; "Zinc Ions Induce the Unfolding and Self-Association of Boar Spermadhesin PSP-I, a Protein With a Single CUB Domain Architecture, and Promote Its Binding to Heparin"; Article, May 2006, pp. 8227-8235, vol. 45, American Chemical Society, Biochemistry (9 pages).
Campanero-Rhodes, Maria Asuncion, et al.; "Analysis of the Stability of the Permadhesin PSP-I/PSP-II Heterodimer"; Article, 2005, pp. 5663-5670, vol. 272, Federation of European Biochemical Societies (8 pages).
Centurion, Fernando, et al.; "Influence of Porcine Spermadhesins on the Susceptibility of Boar Spermatozoa to High Dilution"; Article, Apr. 2003, vol. 69, Biology of Reproduction (7 pages).
de Graaf, S. P., et al.; "Application of Seminal Plasma in Sex-Sorting and Sperm Cryopreservation"; Article, Jul. 2008, pp. 1360-1363, vol. 70, Theriogenology (4 pages).
Ekhlasi-Hundrieser, Mahnaz, et al.; "Point Mutations Abolishing the Mannose-Binding Capability of Boar Spermadhesin AQN-1"; Article, Feb. 2008, pp. 856-862, vol. 1784, Elsevier B.V., Biochimica et Biophysica Acta (7 pages).
Garcia, E. M., et al.; "Distinct Effects of Boar Seminal Plasma Fractions Exhibiting Different Protein Profiles on the Functionality of Highly Diluted Boar Spermatozoa"; Article, 2009, pp. 200-205, vol. 44, Reproduction of Domestic Animals (6 pages).
Garcia, E. M., et al.; "Localization and Expression of Spermadhesin PSP-I/PSP-II Subunits in the Reproductive Organs of the Boar"; Article, 2007, pp. 408-417, vol. 31, International Journal of Andrology (10 pages).
Garcia, E. M., et al.; "Improving the Fertilizing Ability of Sex Sorted Boar Spermatozoa"; Article, May 2007, pp. 771-778, vol. 68, Theriogenology (8 pages).
Garcia, Eva M., et al.; "Dissecting the Protective Effect of the Seminal Plasma Spermadhesin PSP-I/PSP-II on Boar Sperm Functionality"; Article, Jun. 2006, pp. 434-443, vol. 27, No. 3, Journal of Andrology (10 pages).
Jonakova, V., et al.; "Separation, Characterization and Identification of Boar Seminal Plasma Proteins"; Article, Oct. 2006, pp. 307-314, vol. 849, Journal of Chromatography B (8 pages).
Jonakova, Vera, et al.; "Sperm Surface Proteins in Mammalian Fertilization"; Article, 2000, pp. 275-277, vol. 56, Molecular Reproduction and Development (3 pages).
Kwok, Simon C.M., et al.; "Binding Characteristics and Immunolocalization of Porcine Seminal Protein, PSP-I"; Article, 1993, pp. 244-250, vol. 35, Molecular Reproduction and Development (7 pages).
Leshin, L. S., et al.; "Immunostimulatory Effects of Pig Seminal Proteins on Pig Lymphocytes"; Article, 1998, pp. 77-84, vol. 114, Journal of Reproduction and Fertility (8 pages).
Liberda, Jiri, et al.; "Saccharide-Mediated Interactions of Boar Sperm Surface Proteins With Components of the Porcine Oviduct"; Article, 2006, pp. 112-125, vol. 71, Journal of Reproductive Immunology (14 pages).
Manaskova, P., et al.; "Localization of Porcine Seminal Plasma (PSP) Proteins in the Boar Reproductive Tract and Spermatozoa"; Article, 2008, p. 40-48, vol. 78, Journal of Reproductive Immunology (9 pages).
Manaskova, Pavla, et al.; "Mutual Interactions of Boar Seminal Plasma Proteins Studied by Immunological and Chromatographic Methods"; Article, 2003, pp. 399-410, vol. 50, American Journal of Reproductive Immunology (12 pages).
Manaskova, Pavla, et al.; "Characterization of Proteins From Boar Prostate"; Article, 2002, pp. 283-290, vol. 48, American Journal of Reproductive Immunology (8 pages).
Manaskova, Pavla, et al.; "Isolation of Non-Heparin-Binding and Heparin-Binding Proteins of Boar Prostate"; Article, 2002, pp. 137-143, vol. 770, Journal of Chromatography B (7 pages).
Manaskova, P., et al.; "Aggregated and Monomeric Forms of Proteins in Boar Seminal Plasma: Characterization and Binding Properties"; Article, 2000, pp. 143-151, vol. 46, Folia Biologica (Praha) (3 pages).
Nimtz, Manfred, et al.; "Structural Characterization of the Oligosaccharide Chains of Native and Crystallized Boar Seminal Plasma Spermadhesin PSP-I and PSP-II Glycoforms"; Article, 1999, pp. 703-718, vol. 265, European Journal of Biochemistry, Federation of European Biochemical Societies (16 pages).
Rodriguez-Martinez, Heriberto, et al.; "Boar Spermatozoa in the Oviduct"; Article, 2005, pp. 514-535, vol. 63, Theriogenology (22 pages).
Romero, A., et al.; "X-Ray Crystallographic Analysis of Boar PSP-I/PSP-II Complex"; Article, 1997, pp. 311-312; vol. 53, The Fate of the Male Germ Cell, Plenum Press New York (2 pages).
Romero, Antonio, et al.; "Crystallization and Preliminary X-ray Diffraction Analysis of Boar Seminal Plasma Spermadhesin PSP-I/PSP-II, a Heterodimer of Two CUB Domains"; Article, 1996, pp. 15-17, vol. 382, Federation of European Biochemical Societies (3 pages).
Solis, Dolores, et al.; "Binding of Mannose-6-Phosphate and Heparin by Boar Seminal Plasma PSP-II, a Member of the Spermadhesin Protein Family"; Article, 1998, pp. 273-278, vol. 431, Federation of European Biochemical Societies (6 pages).
Solis, Dolores, et al.; "Fractionation and Characterization of Boar Seminal Plasma Spermadhesin PSP-II Glycoforms reveal the Presence of Uncommon N-acetylgalactosamine-Containing N-linked Oligosaccharides"; Article, 1997, pp. 275-280, vol. 14, Glycoconjugate Journal Chapman & Hall (6 pages).
Varela, Paloma F., et al.; "The 2.4 A Resolution Crystal Structure of Boar Seminal Plasma PSP-I/PSP-II: a Zona Pellucida-Binding Glycoprotein Heterodimer of the Spermadhesin Family Built by a CUB Domain Architecture"; Article, 1997, pp. 635-649, vol. 274, Journal of Molecular Biology (15 pages).
Veselsky, L., et al.; "Reverse Effect of Indomethacin on the Immunosuppressive Activity of Boar Seminal Immunosuppressive Fraction"; Article, 2002, pp. 111-123, vol. 71, Animal Reproduction Science (13 pages).
Veselsky, L., et al.; "Inhibition of the Antibody Responses to Rat Blood Transfusion Antigens in Mice by Boar Seminal Immunosuppressive Fraction"; Article, 2000, pp. 325-335, vol. 44, American Journal of Reproductive Immunology (11 pages).
SG Singapore First Written Opinion dated Mar. 26, 2012 issued in corresponding SG Application No. 201102922-0 (7 pages).
Corresponding NZ Patent Application No. 612183; OA mailed Aug. 11, 2014, 2 total pages.
Corresponding AU Patent Application No. 2009295755; OA dated Oct. 30, 2014, 4 total pages.
Grossfeld, R., et al., "Production of pilets with sexed semen employin a non-surgical insemination technique", Theriogenology 63(8) pp. 2269-77, 2005 (Abstract).
Chinese Third Office Action dated Jul. 14, 2014, issued in corresponding CN Application No. 200980147203.0 (5 pp).
Singapore Invitation to Respond to Written Opinion dated Jun. 24, 2014, issued in corresponding SG Application No. 2013055249, 12pp.
Foote. Buffers and Extenders: What do They Do? Why Are They Important? Proc. 10th Tech. Conf. Artif. Insem. Reprod, 1984, pp. 62-70.
IMV Technologies. Biotechnologies for Pig Reproduction. Website www.omv-technologies.com, originally downloaded Aug. 6, 2012, 28 total pages.
Minitube of America. Embryo and Cloning Technologies for Custom Genetic Livestock Production. Website www.usa@minitube.com, originally downloaded Aug. 6, 2012, 1 page.
Corresponding Australian Patent Application No. 2009295755; Office Action dated May 2, 2014, 4 total pages.
Corresponding Australian Patent Application No. 2009295755; Office Action dated Jan. 30, 2015, 4 total pages.

(56) References Cited

OTHER PUBLICATIONS

Corresponding Canadian Patent Application No. 2,742,409; Office Action dated Oct. 2, 2014, 3 total pages.
Corresponding Singapore Patent Application No. 203055249; Invitation to Respond to Written Opinion dated Jun. 18, 2015, 12 pages total.
Corresponding Korean Patent Application No. 10-2011-7009488; Notification of Grounds for Refusal dated Jun. 22, 2015, 3 pages total.
Corresponding Chinese Patent Application No. 200980147203.0; Office Action dated Mar. 18, 2015, 7 pages total.
Corresponding European Patent Application No. 09815714.2; Office Action dated Jun. 12, 2015, 3 pages total.

* cited by examiner

DEVICE AND METHOD FOR INSERTING OR OBTAINING A FLUID WITH GAMETES, EMBRYOS OR ANY OTHER TYPE OF SOLUTION IN THE OVIDUCT OF A SOW

CROSS REFERENCED TO RELATED APPLICATIONS

This application is a United States National phase patent application of, and claims the benefit and priority of, International Application No. PCT/ES2009/070402, published on Apr. 1, 2010, filed Sep. 24, 2009, which claims benefit of and priority to Spanish Patent application P200802740 filed Sep. 26, 2008. Each above-mentioned application is hereby incorporated by reference.

TECHNICAL FIELD

The invention described here deals with a device for inserting and/or collecting, by laparoscopic means, fluids which may or may not contain cells, in the oviduct of a sow. The invention enables the successful insertion of a low number of spermatozoids, embryos, or therapeutic solutions inside the oviduct in a brief period of time. The invention can also be applied in any other animal species.

BACKGROUND

No method exists in pig farming for the successful insemination with very low number of spermatozoids or the transfer of embryos in the oviduct, except for a surgical approach by laparotomy. Even so, this is an impracticable method in livestock production. The laparoscopic approach to the genital organs is a technique which has been used since the decade of the 1970's in human beings, when there are disturbances in the passage of spermatozoids through the uterus, or in animal species when there are technical problems in the passage of catheters through the cervix. Among domesticated animals, it is the sheep where the greatest development has occurred. In this context, it has been demonstrated that the depositing of spermatozoids diluted to doses as low as 1 million and 10 million, inseminated in the uterus, makes it possible to achieve good fertility results. Besides reproductive efficiency, in terms of the small number of spermatozoids to be inseminated, laparoscopic insemination offers other advantages. Among these is the possibility of performing explorations of the genital organs at the same time as the insemination, making it possible to visualize the functional changes which are occurring, in particular changes in the ovaries, and being able to detect in this way pathologies which could not be handled by nonsurgical systems. It also makes it possible to homogenize the fertility results over the course of the year, which is not always possible when using other insemination procedures.

In the case of the pig, the nonsurgical procedure of deep intrauterine insemination allows one to successfully deposit spermatozoids in the uterus of a sow down to levels as low as 50 million spermatozoids. There have also been attempts to perform laparoscopic insemination in the uterine horn with at least 20 million spermatozoids, achieving variable fertility results, owing to the characteristics of the uterine wall in this species. Furthermore, this quantity of spermatozoids prevents the insemination of spermatozoids selected by flow cytometry or treated by other technologies where the number of spermatozoids produced per unit of time is extremely low.

Other similar devices are known from the prior art, such as that described in EP 1177776 B1 of the University of Murcia, although the invention presented here has many differences and advantages over the known prior art. The device described in document EP 1177776 B1 is a nonsurgical device that is introduced via the vagina, cervix, and body of the uterus until it reaches the depths of the uterine horn as the deepest anatomical location. The number of spermatozoids inseminated should be at least 50 million spermatozoids in order to achieve success in the fecundation.

SUMMARY OF THE INVENTION

The invention describes a device for inserting of fluids, which may or may not contain cells, in the oviduct of a sow, making it possible to introduce spermatozoids, embryos, or any type of therapeutic solution, and obtain a fluid with or without cells (gametes—spermatozoids and/or ovocytes—and embryos) from the interior of the oviduct. The device comprises a rigid tubular body that is introduced by a laparoscopic trocar and makes it possible to introduce a flexible tube through its inside, having the following principal characteristics:

the rigid tubular body and the interior flexible tube are coaxial,
the interior flexible tube is connected at the proximal end to a beveled needle,
the flexible tube allows the beveled needle to be inserted in the oviduct, at an angle of 45 degrees,
the distal end of the flexible tube is connected by one or more sheaths closed by one or more pistons, which slide(s) through the inside of the sheath(s), and enable(s) the precise introduction of fluids with low volume.

The tubular body of the device for inserting fluids into the oviduct of a sow is in turn covered by a sterile case. In another alternative configuration, this sterile case is disposable.

In another alternative configuration, the distal end of the flexible tube of the described device is connected to two sheaths, each closed by a piston, which slides inside the sheaths, the two sheaths being connected to the flexible tube by a double cock, alternately enabling the passage of the fluids contained in each sheath.

Evacuation of the device is done by unlocking the sheath(s), pulling back the beveled needle into the lumen of the rigid tubular body.

The invention also describes a procedure for inserting fluids, with or without cells, in the oviduct of a sow by using the device of the invention. The procedure makes it possible to introduce spermatozoids, embryos or any type of therapeutic solution in the oviduct of the sow, or to obtain gametes (spermatozoids and/or ovocytes), embryos, or any type of solution from inside the oviduct of a sow. In this procedure, one introduces the device into the oviduct of the sow in the proximal region of the oviduct ampoule, from which the gametes, embryos and/or solutions are discharged gently and without difficulty.

In this procedure for introducing a fluid with spermatozoids, embryos or therapeutic solutions inside the oviduct of a sow, the beveled injection needle is oriented from the ampoule of the oviduct toward the isthmus of the oviduct.

This procedure for introducing fluids, with or without cells, in the oviduct of a sow makes it possible to verify the correct visualization of the inoculation by means of the temporary dilation of the walls of the oviduct.

A procedure is also described for transfer of embryos in a stage from the zygote to the 4-blastomere stage in the oviduct of a sow, using a device with a double-sheath system, making it possible to introduce separately the fluids contained in each of these sheaths.

BRIEF DESCRIPTION OF THE DRAWINGS

In order to provide a better understanding of this specification, as an integral part of same, we present a series of drawings showing the subject of the invention in illustrative and nonlimiting manner.

Figure 1:
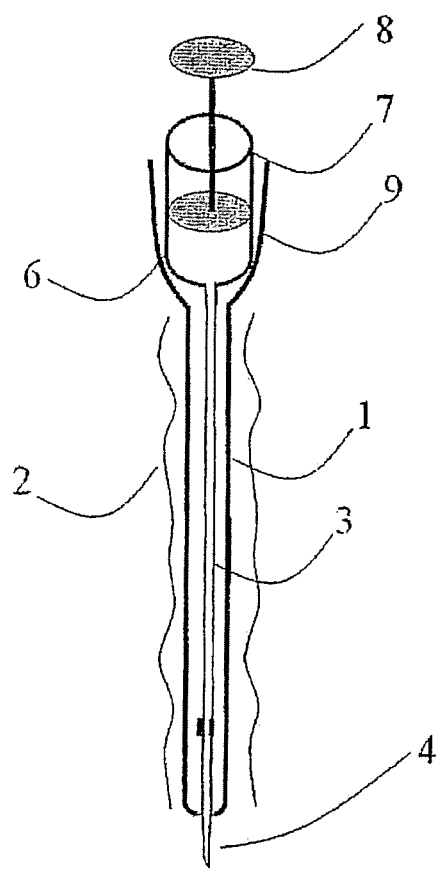
FIG. 1 shows in elevated side view the device of the invention, showing the distinct elements of which it is composed.

In the drawings, the following reference numbers are related to the corresponding elements mentioned hereinafter:
1—Rigid tubular body.
2—Sterile case.
3—Flexible tube.
4—Beveled needle.
5—Oviduct ampoule.
6—Sheath/piston device.
7—Sheath.
8—Piston.
9—Posterior end of the flexible tube (3).
10—Viewing system.
11—Forceps.
12—Oviduct.
13—Double sheath.
14—Double cock.
15—First sheath.
16—Second sheath.

BEST MODES FOR CARRYING OUT THE INVENTION

To solve the drawbacks pointed out in the prior art, the invention develops a new device and procedure making it possible to introduce a fluid, with or without cells, in the oviduct of a sow in the Trendelenburg position and under general anesthesia, at the side where fertilization occurs.

For this, the procedure of the invention involves minor surgery performed under general anesthesia with an incision of 2 cm in the umbilical region. Through this, a trocar with direct viewing is introduced to commence producing the pneumoperitoneum. After this, CO2 is introduced to produce the pneumoperitoneum at a pressure of 2 atmospheres via a tube of 2 mm diameter, ending at the trocar. The introduction of the gas is done for a maximum period of 10-15 seconds.

It invention is composed of a rigid tubular body (1), inside which runs a flexible tube (3) whose base is connected to a beveled needle (4). The other end is connected to a device (6) comprising a sheath (7) closed by a piston (8) that slides inside the sheath (7) and allowing a precision introduction of low-volume liquids. This body (1) is in turn covered by a sterile case (2), allowing it to be used in different animals; said sterile case (2) can be disposable. The above-described characteristics of flexibility of the tube and diameter and length of the needle make it possible to deposit the fluids, with or without cells, safely inside the oviduct (12). Moreover, the dilation of the oviduct walls during the time of the insemination confirms the proper deposition of the fluid.

To bring about the introduction of the fluid, or its extraction as the case may be, the animal is subjected to what is known as a minimally invasive surgical procedure. For this, as already mentioned, an incision of around 2 cm length in the skin of the abdominal region is made in the sow in the Trendelenburg position and under general anesthesia. After introducing a viewing system (10), such as that illustrated in FIG. 3, one proceeds to introduce a sufficient quantity of CO2 in the abdominal cavity of the animal, making it possible to visualize the organs. This process of introducing gas is done directly at a pressure of around 2 atmospheres. Once the condition of the inside of the abdominal cavity has been verified, one proceeds to introduce two accessory trocars in the flanks of the animal. The first of these will serve to introduce a nontraumatic forceps (11) to assist in the manipulating and holding of the oviduct (12). The second serves to introduce the specific instrument of the invention.

The instrument for insemination, transfer of embryos or introducing of fluids that is necessary to carry out the procedure consists of an injection system, which is comprised of a rigid external tubular body (1) which, being adjusted to the existing trocar, allows it to be inserted into the abdominal cavity of the sow. This tubular body (1) is in turn covered by a sterile case (2), which allows it to be used in different animals. A flexible tube (3) runs coaxially, whose proximal end connects to a beveled needle (4) that allows it to be inserted at an angle of 45 degrees in the oviduct (12), and more specifically in the vicinity of the oviduct ampoule (5). The distal end of the flexible tube connects to a device comprising a sheath (7), closed at the other end by a piston (8), which slides inside the sheath (7), and enables the precision introduction of low-volume liquids.

When the device is used in the mode of insemination with very low number of spermatozoids, one proceeds to fill the sheath/piston device (6), which comprises the sheath (7) closed by the piston (8), which slides inside the sheath (7), and enables the precision introduction of low-volume liquids. Once the sheath/piston device (6) has been filled, it is connected to the posterior end of the flexible tube (3) coaxially to the rigid tubular body (1), proceeding with the filling of the latter. The whole is inserted by the trocar, arranged for this purpose until the anterior end of the rigid tubular body (1) is situated in the vicinity of the oviduct ampoule (5), then moving the coaxial flexible tube (3) until the sheath (7) located at the posterior end (9) of the flexible tube is totally locked in the rigid tubular body (1). This arrangement enables an easy insertion of the beveled needle (4) in the lumen of the oviduct by using an access angle of 45 degrees.

Figure 3:
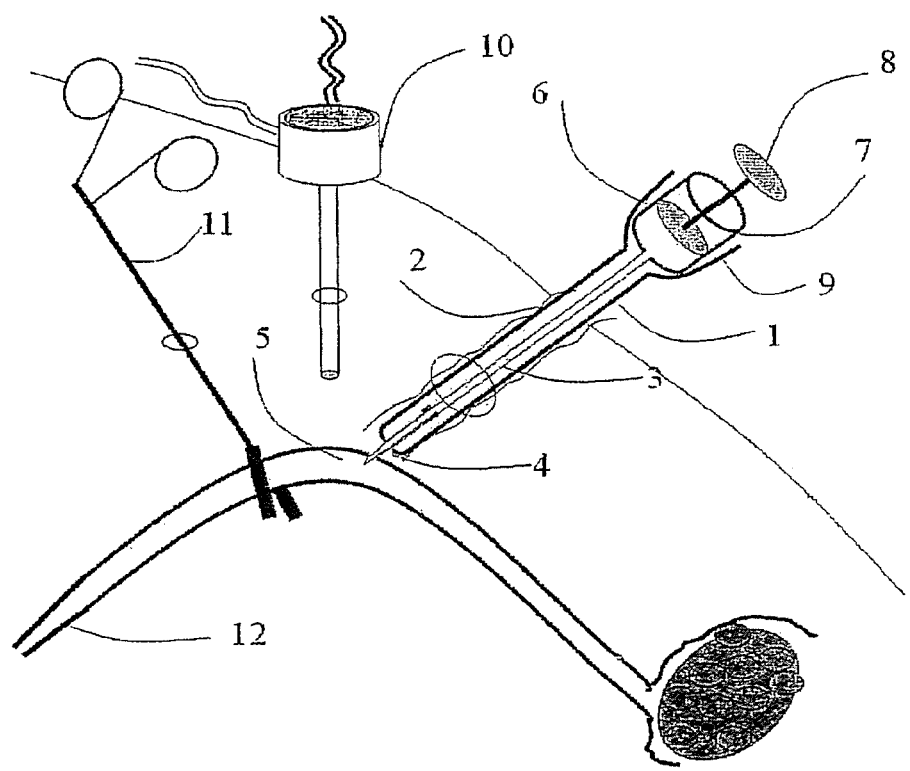
FIG. 3 shows a schematic representation of the device of the invention in working state inside the abdominal cavity of a sow.

The point of access to the oviduct should occur in the oviduct ampoule (5), the end of the needle being oriented toward the isthmus of the oviduct (12), as shown in FIG. 3. The characteristics of the device reduce the risk of accidents from perforation of the opposite wall of the oviduct. Once the flexible tube (3) is in communication with the oviduct ampoule (5) via the needle (4), one proceeds to move the piston (8) on the sheath (7), discharging the predetermined volume of fluid. The proper discharging of the fluid is verified by observing a temporary dilation of the walls of the oviduct (12) in general and of the oviduct ampoule (5) in particular.

The evacuation of the system is done by unlocking the sheath (7), making it possible to conceal the beveled needle (4) inside the rigid tubular body (1), avoiding possible accidents in adjacent areas. The recovery of the sow occurs in the following minutes. The use of this procedure makes it possible to repeat the insemination in the same female in consecutive cycles.

Figure 2:
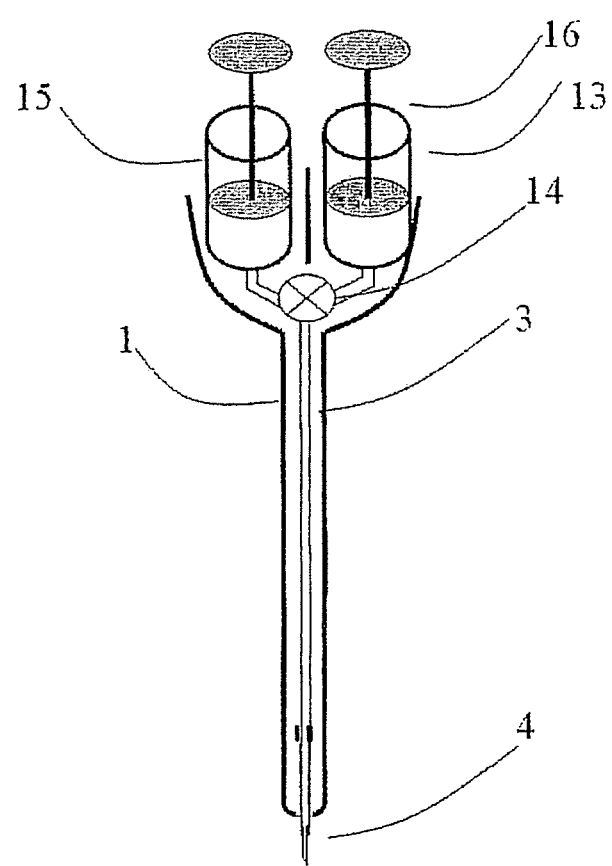
FIG. 2 is an elevated side view of the device of the invention, adapted for the transfer of embryos.

When the device is used in embryo transfer mode, the system includes two sheaths, a first sheath (15) and a second sheath (16), each closed by its own piston, and connected to the flexible tube (3) by means of a double cock system (14), as can be seen in FIG. 2; in this case, the sterile case (2) is not shown. One proceeds to fill the flexible tube (3) by the opening that connects the sheath containing only the embryo transfer medium, which is contained, for example, in the first sheath (15). As can be seen from FIG. 3, the device is introduced by the trocar, arranged for this purpose until the anterior end of the rigid tubular body (1) is in the vicinity of the oviduct ampoule (5), then moving the coaxial flexible tube (3) until total locking of the double sheath system and it is situated in the posterior end of the flexible tube (3) in the rigid tubular body (1).

One then proceeds to close the sheath containing the embryo transfer medium, for example, the first sheath (15), and open the sheath containing the embryos, for example, the second sheath (16), which are going to be transferred in a total volume of 100-200 µl. The embryos being transferred should be between the development stage of the zygote to the 4-blastomere stage. The point of access to the oviduct should be in the oviduct ampoule (5), the tip of the needle (4) being oriented toward the isthmus of the oviduct (12). The characteristics of the device reduce the risk of accidents from perforation of the opposite wall of the oviduct.

Once the flexible tube (3) is in communication with the lumen of the oviduct via the needle (4), one proceeds to move the piston (8) on the sheath that contains the embryos, for example, the second sheath (16), discharging the volume of fluid contained therein. The proper discharging of the fluid is verified by observing a temporary dilation of the walls of the oviduct ampoule (5). After this, one proceeds to close the sheath containing the embryos, for example, the second sheath (16), and open the sheath containing the embryo transfer medium, for example, the first sheath (15), in order to discharge an additional volume of 100 µl, allowing the embryos to move from the lumen of the flexible tube (3) to the interior of the oviduct (12). Evacuation of the system is done by unlocking the double sheath system, making it possible to conceal the beveled needle (4) in the lumen of the rigid tubular body (1), avoiding possible accidents in adjacent areas. The recovery of the sow occurs in the following minutes. This procedure makes it possible to repeat the transfers in the same female in consecutive cycles.

The invention claimed is:

1. A device for inserting or removing fluids in an oviduct of a sow, comprising:
   a rigid tubular body;
   a flexible tube having opposing flexible tube proximal and distal ends, the flexible tube located coaxially through the rigid tubular body,
   wherein the flexible tube proximal end connects to a beveled needle,
   wherein coaxial movement of the flexible tube within the rigid tubular body allows the beveled needle to be inserted in the oviduct when the rigid tubular body is located in the vicinity of the oviduct;
   one or more sheaths directly connected or connected through a double cock to the flexible tube distal end; and
   one or more pistons closing the one or more sheaths, wherein the one or more pistons slide one each through the inside of the one or more sheaths; wherein the rigid tubular body has a configuration which locks the one or more sheaths at a location in the rigid tubular body with the beveled needle extended outside of the rigid tubular body, and wherein evacuation of the device is done by unlocking the one or more sheaths pulling the beveled needle back into the rigid tubular body.

2. The device of claim 1, wherein the rigid tubular body is covered by a sterile case.

3. The device of claim 2, wherein the sterile case is disposable.

4. The device of claim 1, wherein the one or more sheaths comprise two sheaths and the one or more pistons comprise two pistons, each of the two sheaths closed by one of the two pistons which slides inside the two sheaths, the two sheaths being connected to the flexible tube by said double cock, alternately enabling passage of the fluids contained in each one of the two sheaths to the distal end of the flexible tube.

5. The device of claim 1, wherein the fluids to be inserted or removed are selected from the group consisting of: spermatozoids, embryos, oocytes, ovocytes, and therapeutic solutions.

6. The device of claim 1, wherein the fluids removed from the oviduct include cells.

7. The device of claim 1, wherein the fluids removed from the oviduct do not include cells.

8. A method of inserting or removing fluids in an oviduct of a sow comprising:
   introducing a rigid tubular body through an abdominal region of the sow;
   coaxially locating a flexible tube having opposing flexible tube proximal and distal ends through the rigid tubular body, wherein the flexible tube proximal end connects to a beveled needle;
   inserting the beveled needle into a lumen of the oviduct of the sow;
   actuating one or more pistons each correspondingly closing one or more sheaths directly connected to the flexible tube distal end, wherein each of the one or more pistons correspondingly slide though the inside of the one or more sheaths for inserting or removing the fluids.

9. The method of claim 8, further comprising orienting the beveled needle from an ampoule of the oviduct toward an isthmus of the oviduct.

10. The method of claim 8, further comprising verifying deposition of liquids into the oviduct by visualization of temporary dilation of oviduct walls.

11. The method of claim 8, wherein actuating the one or more pistons each closing the corresponding sheath connected to the flexible tube distal end further comprises:
    actuating a first of the one or more pistons closing a first sheath connected to the flexible tube distal end to introduce a first of the fluids from the first sheath into the oviduct; and
    actuating a second of the one or more pistons closing a second sheath connected to the flexible tube distal end to introduce a second of the fluids from the second sheath into the oviduct.

12. The method of claim 8, further comprising:
    creating a first incision to introduce nontraumatic forceps for holding the oviduct; and
    creating a second incision to introduce a viewing system for visualizing organs of the sow.

\* \* \* \* \*